United States Patent
Brannon

(10) Patent No.: US 10,080,569 B2
(45) Date of Patent: Sep. 25, 2018

(54) SHAPED TIP BURR INSTRUMENT

(71) Applicant: James K Brannon, Leawood, KS (US)

(72) Inventor: James K Brannon, Leawood, KS (US)

( * ) Notice: Subject to any disclaimer, the term of this patent is extended or adjusted under 35 U.S.C. 154(b) by 441 days.

(21) Appl. No.: 14/314,294

(22) Filed: Jun. 25, 2014

(65) Prior Publication Data

US 2015/0374397 A1    Dec. 31, 2015

(51) Int. Cl.
| | |
|---|---|
| A61B 17/16 | (2006.01) |
| A61B 17/32 | (2006.01) |
| A61C 3/02 | (2006.01) |
| A61B 17/22 | (2006.01) |

(52) U.S. Cl.
CPC .......... *A61B 17/1633* (2013.01); *A61B 17/16* (2013.01); *A61B 17/1613* (2013.01); *A61B 17/1615* (2013.01); *A61B 17/32* (2013.01); *A61B 17/32002* (2013.01); *A61B 17/320016* (2013.01); *A61C 3/02* (2013.01); *A61B 2017/1602* (2013.01); *A61B 2017/22079* (2013.01); *A61B 2017/320084* (2013.01); *A61B 2217/005* (2013.01)

(58) Field of Classification Search
CPC ............ A61B 17/16; A61B 2017/1602; A61B 17/1613; A61B 17/1615; A61B 17/1633; A61B 17/32; A61B 17/320016; A61B 17/32002; A61B 2017/320084; A61B 2217/005; A61C 3/02

See application file for complete search history.

(56) References Cited

U.S. PATENT DOCUMENTS

| | | | | |
|---|---|---|---|---|
| 4,389,192 A | * | 6/1983 | Neuwirth | A61C 3/02 433/166 |
| 5,913,867 A | * | 6/1999 | Dion | A61B 17/32002 606/170 |
| 6,053,923 A | * | 4/2000 | Veca | A61B 17/32002 606/79 |
| 7,077,845 B2 | * | 7/2006 | Hacker | A61B 17/32002 606/180 |

FOREIGN PATENT DOCUMENTS

GB    1132876 A  *  11/1968  ............. A61C 3/02

OTHER PUBLICATIONS

U.S. Appl. No. 10/928,553, filed Aug. 26, 2004, James Kevin Brannon.
U.S. Appl. No. 11/970,246, filed Jan. 7, 2008, James K. Brannon.
U.S. Appl. No. 12/369,388, filed Feb. 11, 2009, James K. Brannon.
(Continued)

*Primary Examiner* — Larry E Waggle, Jr.
(74) *Attorney, Agent, or Firm* — Arthur K Shaffer; Intellectual Property Center, LLC

(57) ABSTRACT

An improved motorized burr instrument for operation on tissue at a desired surgical site surrounding by fluid, the motorized burr instrument being operable with a variable speed motor at a rotary drive coupler with a hub extending therefrom, an outer sheath housing a rotating member extending between the rotary drive coupler and a burr having a cutting edge with at least one radial projection joining a leading and a trailing edge and rotating said fluid through the outer sheath as the cutting edge is rotated.

6 Claims, 4 Drawing Sheets

(56) References Cited

OTHER PUBLICATIONS

U.S. Appl. No. 12/181,205, filed Jul. 28, 2008, James K. Brannon.
U.S. Appl. No. 12/369,575, filed Feb. 11, 2009, James K. Brannon.
U.S. Appl. No. 12/706,706, filed Feb. 6, 2010, James K. Brannon.
U.S. Appl. No. 13/361,823, filed Jan. 30, 2012, James K. Brannon.
U.S. Appl. No. 61/170,508, filed Apr. 17, 2009, James K. Brannon.
U.S. Appl. No. 61/253,068, filed Oct. 20, 2009, James K. Brannon.
U.S. Appl. No. 61/218,757, filed Jun. 19, 2009, James K. Brannon.
U.S. Appl. No. 29/340,631, filed Jul. 22, 2009, James K. Brannon.
U.S. Appl. No. 61/266,908, filed Dec. 4, 2009, James K. Brannon.
U.S. Appl. No. 61/266,900, filed Dec. 4, 2009, James K. Brannon.
U.S. Appl. No. 61/303,496, filed Feb. 11, 2010, James K. Brannon.
U.S. Appl. No. 61/303,508, filed Feb. 11, 2010, James K. Brannon.
U.S. Appl. No. 61/309,732, filed Mar. 2, 2010, James K. Brannon.
U.S. Appl. No. 61/319,166, filed Mar. 30, 2010, James K. Brannon.
U.S. Appl. No. 61/325,084, filed Apr. 16, 2010, James K. Brannon.
U.S. Appl. No. 61/325,102, filed Apr. 16, 2010, James K. Brannon.
U.S. Appl. No. 12/763,213, filed Apr. 20, 2010, James K. Brannon.
U.S. Appl. No. 12/820,133, filed Jun. 21, 2010, James K. Brannon.
U.S. Appl. No. 12/908,879, filed Oct. 21, 2010, James K. Brannon.
U.S. Appl. No. 12/961,487, filed Dec. 6, 2010, James K. Brannon.
U.S. Appl. No. 12/961,491, filed Dec. 6, 2010, James K. Brannon.
U.S. Appl. No. 12/986,064, filed Jan. 6, 2011, James K. Brannon.
U.S. Appl. No. 61/443,655, filed Feb. 16, 2011, James K. Brannon.
U.S. Appl. No. 61/444,025, filed Feb. 17, 2011, James K. Brannon.
U.S. Appl. No. 61/444,315, filed Feb. 18, 2011, James K. Brannon.
U.S. Appl. No. 61/645,327, filed May 23, 2012, James K. Brannon.
U.S. Appl. No. 29/398,708, filed Aug. 3, 2011, James K. Brannon.
U.S. Appl. No. 13/444,559, filed Apr. 11, 2012, James K. Brannon.
U.S. Appl. No. 13/039,191, filed Mar. 2, 2011, James K. Brannon.
U.S. Appl. No. 13/076,408, filed Mar. 20, 2011, James K. Brannon.
U.S. Appl. No. 13/089,306, filed Apr. 18, 2011, James K. Brannon.
U.S. Appl. No. 13/197,476, filed Aug. 3, 2011, James K. Brannon.
U.S. Appl. No. 29/445,846, filed Feb. 18, 2013, James K. Brannon.
U.S. Appl. No. 13/838,330, filed Mar. 15, 2013, James K. Brannon.
U.S. Appl. No. 29/449,726, filed Mar. 15, 2013, James K. Brannon.
U.S. Appl. No. 13/844,852, filed Mar. 15, 2013, James K. Brannon.
U.S. Appl. No. 29/449,928, filed Mar. 15, 2013, James K. Brannon.
U.S. Appl. No. 29/450,070, filed Mar. 15, 2013, James K. Brannon.
U.S. Appl. No. 61/839,152, filed Jun. 25, 2013, James K. Brannon.
U.S. Appl. No. 13/944,696, filed Jul. 17, 2013, James K. Brannon.
U.S. Appl. No. 61/891,836, filed Oct. 16, 2013, James K. Brannon.

* cited by examiner

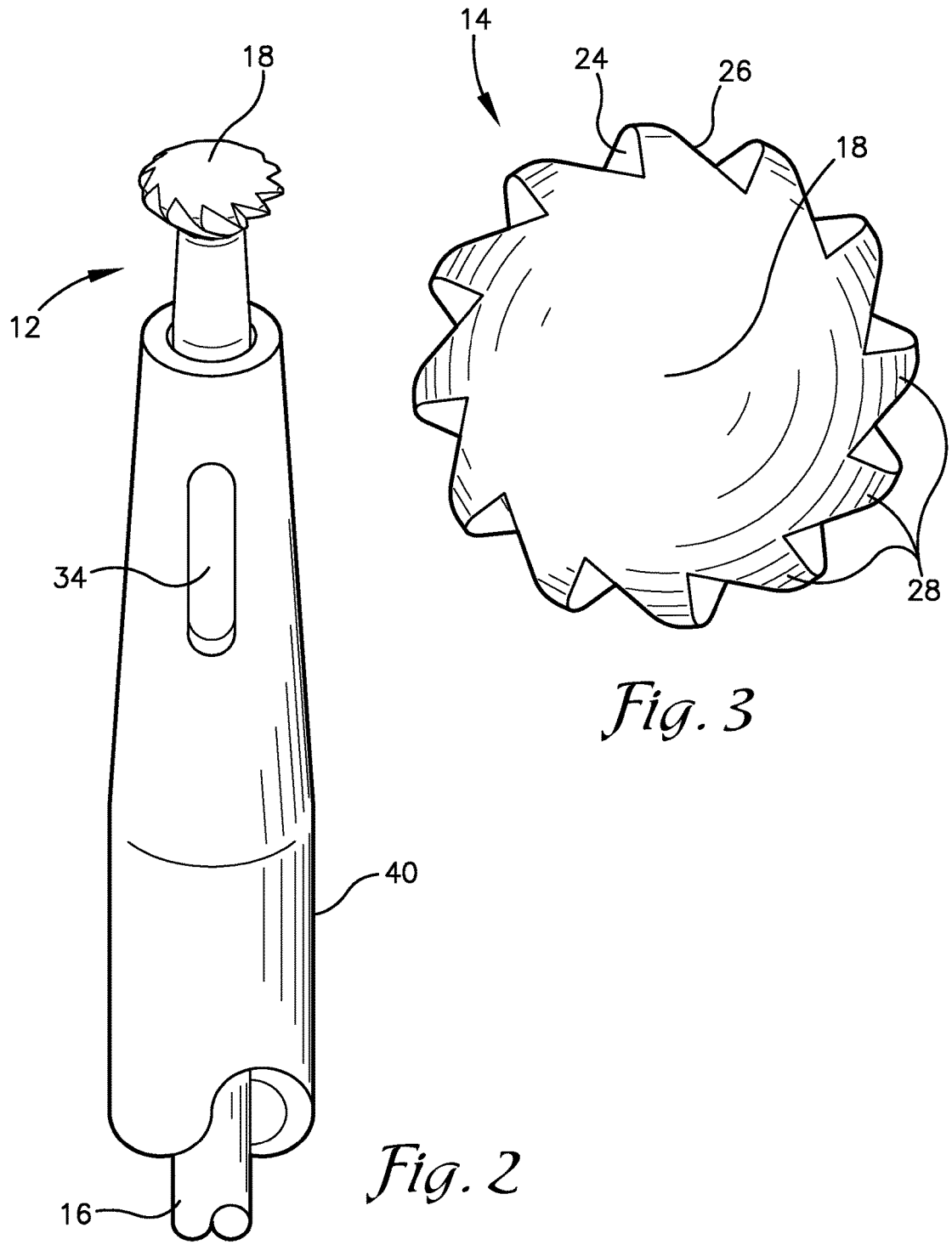

SHAPED TIP BURR INSTRUMENT

CROSS-REFERENCE TO RELATED APPLICATION

This application is a non-provisional application claiming the benefit of the prior filed U.S. provisional application No. 61/839,152, filed Jun. 25, 2013 which is incorporated herein by reference.

FIELD OF THE INVENTION

The present invention is broadly directed to improvements in instruments for arthroscopic surgery and, more particularly, to a rotary abrader which provides an improved extraction of debris from the surgical site during arthroscopic procedures.

BACKGROUND OF THE INVENTION

Modern surgery tends toward minimally invasive techniques whenever possible because they reduce pain and accelerate healing. Although often more complicated in some ways for the surgeon, minimally invasive techniques result in less trauma to the patient and less scarring because of much smaller incisions thereby promoting faster healing and reducing possibilities for infections. In general, minimally invasive surgeries involve making one or more small incisions at appropriate locations and inserting tubular devices through the incisions to the surgical site. Arthroscopic surgery, which typically occurs in an inter-articular space filled with fluid, allows orthopedists to efficiently perform procedures, including abrading and shaping both soft and hard tissue such as bone, cartilage and ligaments using special purpose tools designed specifically for arthroscopists. Among these instruments are graspers, biters, shavers and burrs. Many of these instruments include a hollow center and are coupled to a base connectable to a motor for operation of the instrument. Some of the instruments also include a rotatable inner tube having an abraded head at its distal end and fixed to an outer tube for rotational removal of the tissue. The space between the inner and outer tube is typically limited. As the tissue is being abraded, debris and fluid are generally drawn or sucked through the rotatable inner shaft which supports the burr. However, because the space is limited, debris can becomes lodged within the space between the outer and inner tube clogging up the instrument, causing poor visual clarity of the surgical site.

During use, some burrs are designed to fit through a small cannulae, which allows access to the surgical site. Some surgeons rely upon the cannulae to maintain good visibility with a joint structure. However, for good visibility one must provide for the effective removal of debris, which is continually produced during the abrading process. Providing a small gap within the abrading device for the removal may be inconsistent with this requirement.

Many rotary burrs have teeth or a cutting surface for shaping and removing damaged tissue. However, during use the cutting surface can damage surrounding healthy tissue which is in close proximity with the tissue being removed. The cutting edge of some burrs causes undesired movement, which also damages surrounding tissue. Because of the close proximity of healthy and unhealthy tissue, it is desireable to limit any undesired movement during use.

There is limited room to maneuver within a surgical site. Because of the close proximity, it is desired to maintain accessibility while limiting any visual obstructions from the surgical site. One requirement for good visibility is the effective removal of surrounding debris. Another is that the user have an unobstructed view of the active portion of the abrader in contact with the tissue and an unobstructed view of the tissue as it is abraded by the instrument.

In a typical device, removal of debris from the field is accomplished by aspirating debris from the surgical site via an inner rotating lumen, which is connected to an external vacuum source. However, the manner in which debris and fluid enter the lumen at the distal end of the instrument has a large effect on the volume of flow through the instrument and on the frequency with which the instrument clogs. Insufficient flow causes decreased visibility because of residual debris suspended in the intra-articular fluid. Clogging requires that the instrument be removed from the joint and "de-clogged." The degree of difficulty of clog removal can impact the easy or difficulty of the procedure. Even if clog removal is easily accomplished, repeated removal of the instrument to de-clogging and reinserting the instrument can be problematic and may cause increased procedure times. Aspiration effectiveness, and therefore instrument design, can impact the burr efficiency.

There is a need for an improved burr which provides for improved visibility during surgery while not obstructing the cutting surface. In addition, there is a need for an improved burr with anti-clogging characteristics to improve the removal of debris from the surgical site, which enhances the surgeon's visibility in procedures where visibility is required.

SUMMARY OF THE INVENTION

The present invention is an improved burr with an abrading conical section and a rounded rotary abrader having a clear sheath or hood over the abrading element or burr. The shaft includes a pair of vertically elongated slots provided on the outer cannulated shaft supporting the burr to facilitate aspiration and to help remove debris and fluid extending along the burr and the outer cannulated shaft.

Various objects and advantages of the present invention will become apparent from the following description taken in conjunction with the accompanying drawings wherein are set forth, by way of illustration and example, certain embodiments of this invention. The drawings submitted herewith constitute a part of this specification, include exemplary embodiments of the present invention, and illustrate various objects and features thereof.

BRIEF DESCRIPTION OF THE DRAWINGS

FIG. 2 is partial elevation of the embodiment of FIG. 1.
FIG. 3 is a top plan view of the burr of FIG. 1.

DETAILED DESCRIPTION OF THE INVENTION

Figure 1:
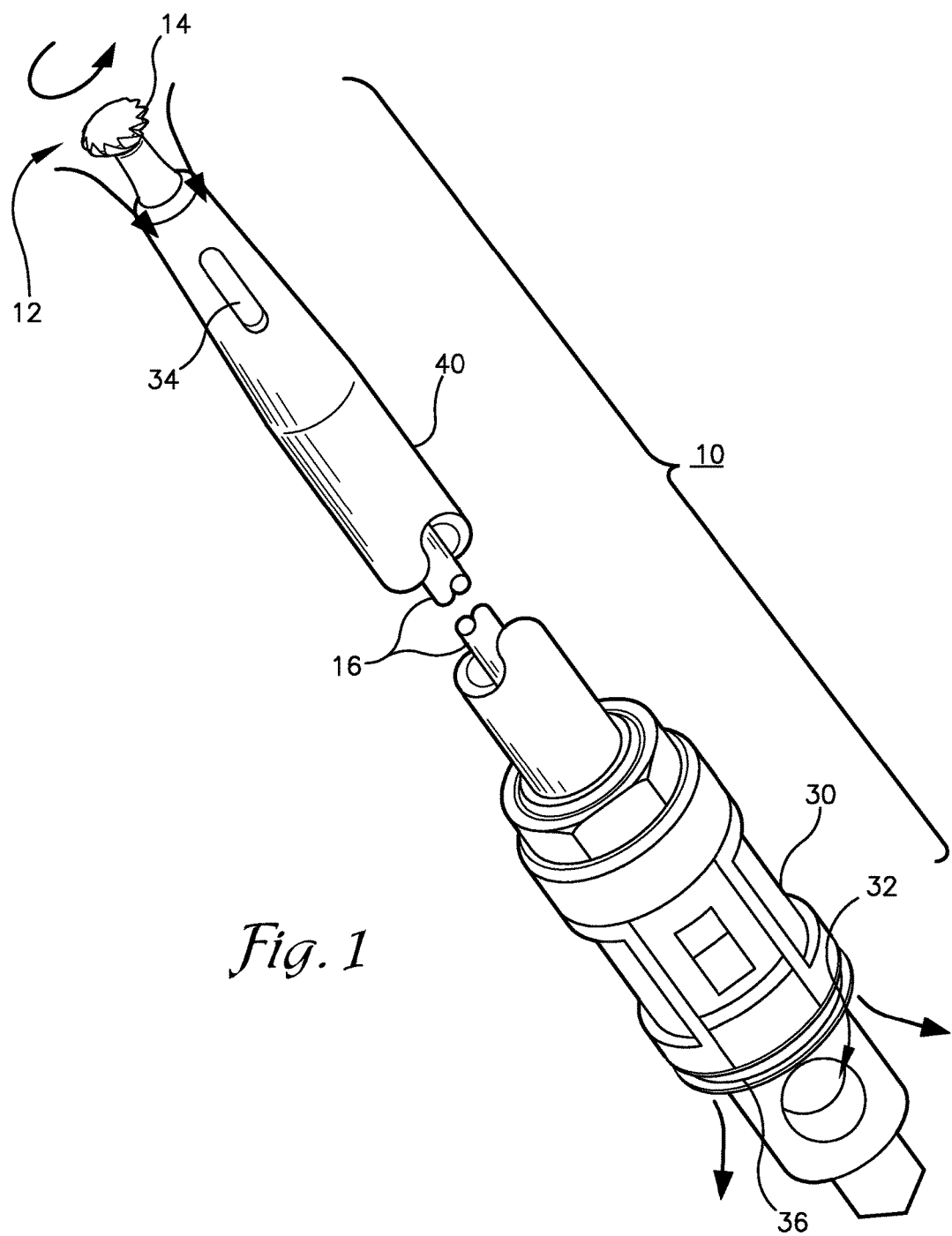
FIG. 1 is a partial side perspective of an embodiment of the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 10 (FIGS. 1-3) generally designates an embodiment of the motorized rotary burr instrument generally referred to herein is in accordance with a first embodiment of the invention. The motor being generally known, is not shown, however the motor consistent with the present invention is a variable speed motor adapted for operation of a burr 12 at a rotary drive coupler 32, depicted in FIG. 1. The rotary drive coupler 32 extends rearwardly from a hub 30.

As depicted in FIGS. 1-3, an embodiment of the burr 12 includes a cutting edge 14 secured to a rotating member 16 adapted for rotation by the motor (not shown) at the coupler 32. The cutting edge 14 is spaced opposite the coupler 32 by the rotational member 16 and includes at least one centrally disposed convex outer surface 18 overlying a frustoconical cutting surface 20 extending towards the rotating member 16 for rotation.

Figure 5:
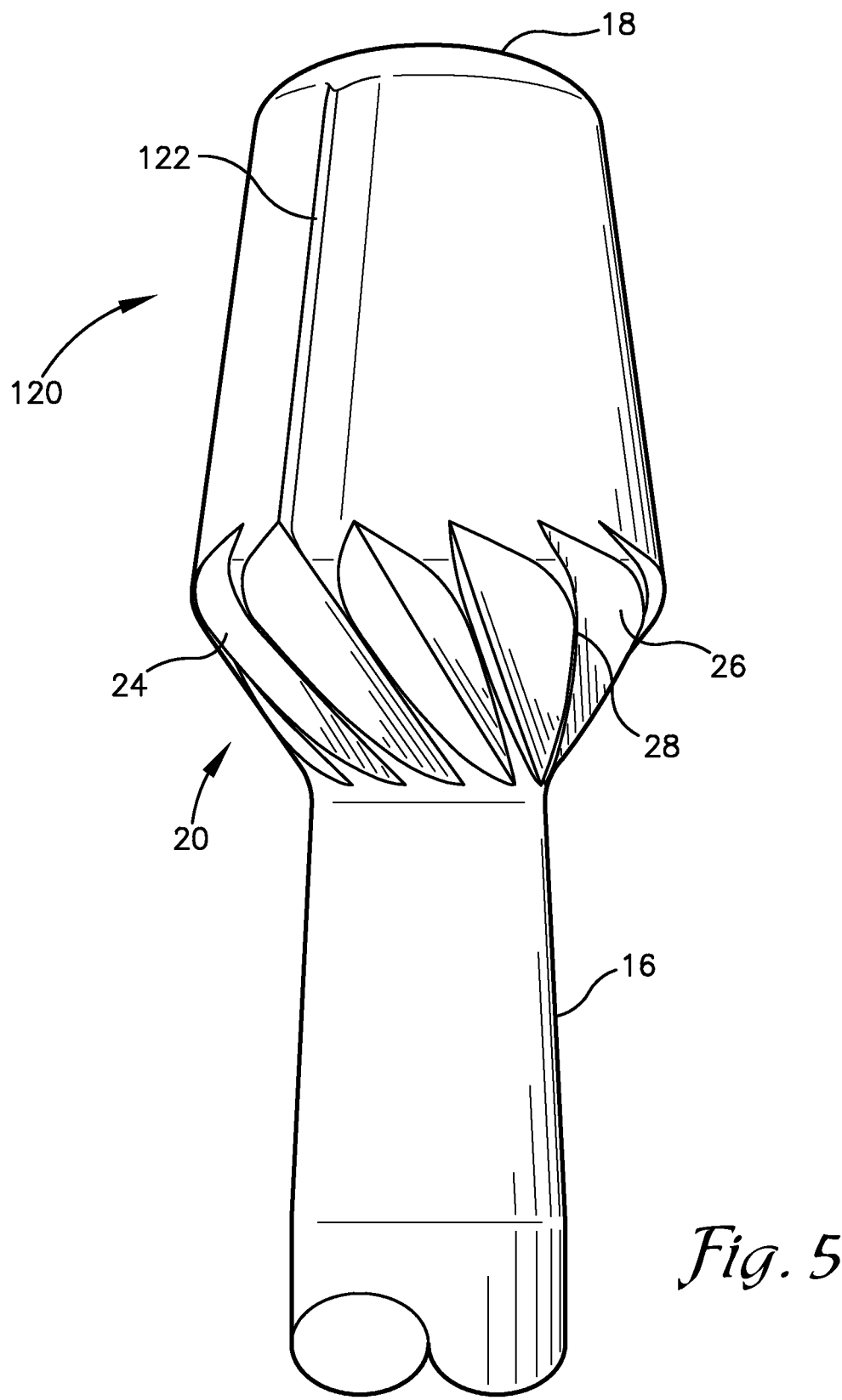
FIG. 5 is a partial side perspective of an alternative burr embodiment.

A second embodiment is depicted in FIG. 5 with a substantially cylindrical surface 120 extending between the frustoconical cutting surface 20 and the convex outer surface 18. The cylindrical surface 120 includes at least one radial projection 122 extending outwardly from the cylindrical surface 120, the radial projection 122 presenting a longitudinal shaving structure extending along the cylindrical surface 120. The longitudinal shaving structure as depicted in FIG. 5 may be used for debriding the desired surgical site.

Figure 4:
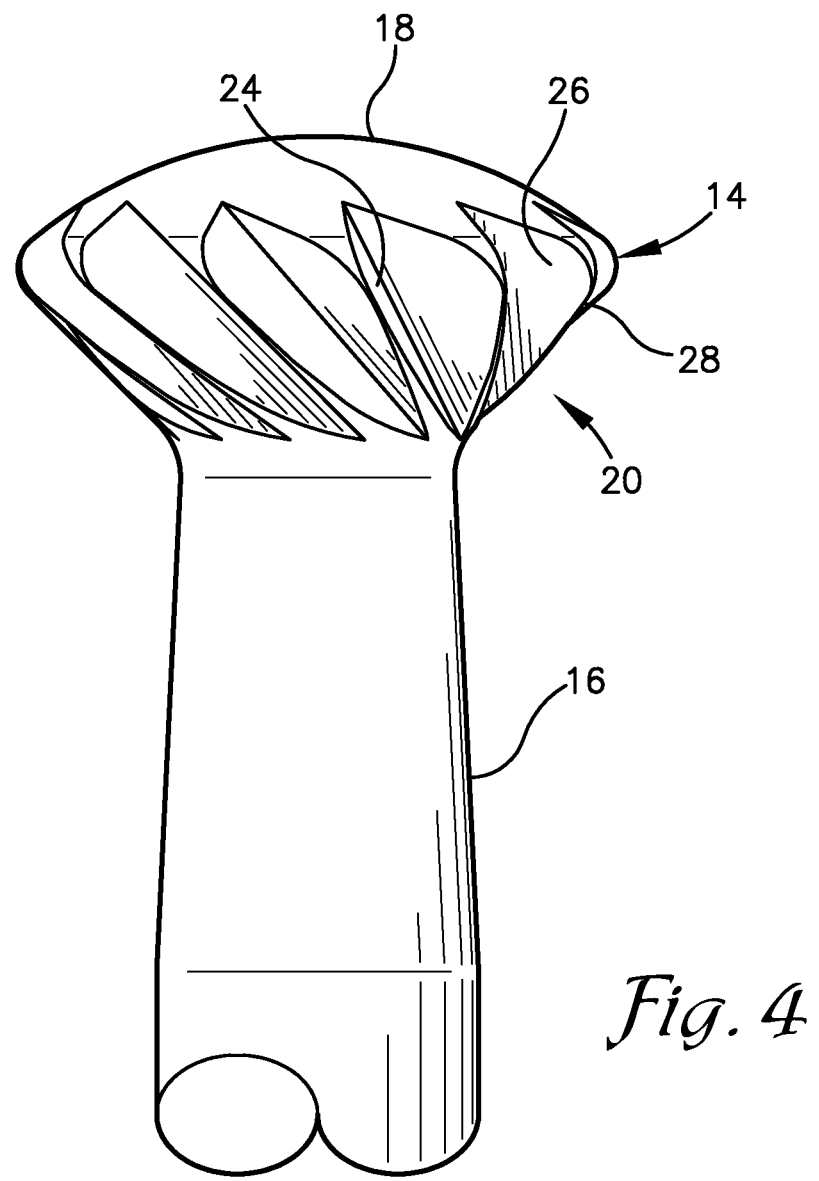
FIG. 4 is a partial side perspective of the burr of FIG. 1.

As depicted in FIGS. 3-4, the frustoconical cutting surface 20 includes a plurality of radial projections or ridges 28 spaced along the cutting surface 20 and extending radially outward. In the embodiment of FIGS. 3-4, each of the projections 28 having a leading 24 and trailing 26 edge joined at the projection/ridge 28 and extending angularly therefrom. When rotated, the projections 28 may present a spiraling force, rotating any surrounding fluid or air (not shown) associated with the surgical site during use. The spiraling force presented by rotation of the projections 28 may form a vortex within the surrounding fluid or air (not shown). Through the rotation of the projections 28, surrounding fluid and any contained surgical debris may by directed downward towards an inlet 34 for passage along the rotating member 16, exiting at outlet 36. The inlet 34 is located along an outer sheath 40 towards the distal end of the rotating member and the outlet 36 extends outwardly from the hub 30 towards the proximate end of the rotating member 16, near the drive coupler 32. Although the inlet 34 is illustrated as an elongated structure in FIG. 1, it could include a number of alternative dimensions or designs for transporting received fluids and affiliated debris therefrom.

It is to be understood that while certain forms of the present invention have been illustrated and described herein, it is not to be limited to the specific forms or arrangement of parts described and shown.

What is claimed and desired to be secured by Letters Patent:

1. An improved motorized burr instrument adapted for removing tissue during operation at a desired surgical site within a surrounding fluid environment with a variable speed motor, wherein said improved motorized burr instrument comprises:
    a rotary drive coupler adapted for operation by said variable speed motor;
    a hub, wherein said rotary drive coupler extends rearwardly from the hub;
    an outer sheath housing a rotating member which extends between said rotary drive coupler and a burr having a cutting edge; and
    said cutting edge including at least one centrally disposed smooth convex outer surface overlying a frustoconical cutting surface inwardly extending from said convex outer surface towards said rotating member, said cutting edge being rotated during operation of said rotary drive coupler and directing fluid through said outer sheath while removing tissue from the desired surgical site;
    wherein said frustoconical cutting surface includes a plurality of substantially parabolic ridges spaced along said cutting surface and joining a leading edge and a trailing edge which taper outwardly from an axis of rotation; and
    an inlet in fluidic communication with an outlet for the passage of fluid therethrough, wherein said inlet is located along said outer sheath.

2. The improved motorized burr instrument of claim 1 that further comprises a substantially cylindrical surface extending between said frustoconical cutting surface and said convex outer surface.

3. The improved motorized burr instrument of claim 2 wherein said substantially cylindrical surface includes at least one radial projection extending outwardly from said substantially cylindrical surface.

4. The improved motorized burr instrument of claim 2 wherein said substantially cylindrical surface further comprises a longitudinal shaving structure extending along said substantially cylindrical surface.

5. The improved motorized burr instrument of claim 1 wherein operation of said cutting edge presents a rotational flow within the surrounding fluid environment.

6. An improved motorized burr instrument adapted for operation within a surrounding fluid environment with a variable speed motor wherein said improved motorized burr instrument comprises:
    a rotary drive coupler adapted for operation by said variable speed motor;
    a hub, wherein said rotary drive coupler extends rearwardly from the hub;
    an outer sheath housing a rotating member which extends between said rotary drive coupler and a burr having a cutting edge;
    said cutting edge including at least one centrally disposed smooth convex outer surface overlying a frustoconical cutting surface inwardly extending from said convex outer surface towards said rotating member, said cutting edge being rotated during operation of said rotary drive coupler and presenting a rotational flow within the surrounding fluid environment;
    wherein said frustoconical cutting surface includes a plurality of substantially parabolic ridges spaced along said cutting surface and joining a leading edge and a trailing edge which taper outwardly from an axis of rotation; and
    an inlet in fluidic communication with an outlet for the passage of fluid therethrough, wherein said inlet is located along said outer sheath.

\* \* \* \* \*